United States Patent [19]

Lee et al.

[11] Patent Number: 5,656,454

[45] Date of Patent: Aug. 12, 1997

[54] ENDOTHELIAL CELL-SPECIFIC ENHANCER

[75] Inventors: Mu-En Lee, Newton; Zhou Fen, Sharon, both of Mass.

[73] Assignee: President and Fellows of Harvard College, Cambridge, Mass.

[21] Appl. No.: 317,333

[22] Filed: Oct. 4, 1994

[51] Int. Cl.$^6$ ................................................. C12N 15/00
[52] U.S. Cl. ...................... 435/69.1; 536/23.5; 536/24.1; 435/320.1; 435/252.3; 435/325; 435/371; 435/354
[58] Field of Search ................................. 536/23.5, 24.1; 435/69.7, 69.1, 69.4, 240.2, 252.3, 320.1

[56] References Cited

U.S. PATENT DOCUMENTS 4,764,504  8/1988  Johnson et al. .............................. 514/12

OTHER PUBLICATIONS

Caskey, "Antisense and Differentiation", Annals Of The New York Academy of Sciences, 660:154–58, Oct. 28, 1992.
Johnston et al., "Cloning of GMP-140, a Granule Membrane Protein of Platelets and Endothelium: Sequence Similarity to Proteins Involved in Cell Adhesion and Inflammation", Cell, 56:1033–44 (1989).
Arceci, R.J., et al., "Mouse Gata-4: a Retinoic Acid–Inducible GATA–Binding Transcription Factor Expressed in Endodermally Derived Tissue and Heart", 1993, Molec. and Cellular Biol., 13(4)2235–46.
Carlos, T.M., et al., "Membrane Proteins Involved in Phagocyte Adherence to Endothelium", 1990, Immunological Revs., 114:5–28.
Cybulsky, M.I., et al., "Endothelial Expression of a Mononuclear Leukocyte Adhesion Molecule During Atherogenesis", 1991, Science, 251:788–91.
Dignam, J.D., et la., "Accurate Transcription Initiation by RNA Polymerase II in a Soluble Extract From Isolated Mammalian Nuclei", 1983, Nucleic Acids Res., 11(5):1475–89.
Diuz, S.M., et al., "Heparin–binding Epidermal Growth Factor–Like Growth Factor Expression in Cultured Fetal Human Vascular Smooth Muscle Cells", 1993, J. Biol. Chem., 268(24):18330–34.
Dorfman, D.M., et al., "Human Transcription Factor GATA–2", 1992, J. Biol. Chem., 267(2):1279–85.
Ghosh, D., "TFD: The Transcription Factors Database", 1992, Nucleic Acids Res., 20:2091–93.
Hansson, G.K., et al., "Interferon γ Inhibits Both Proliferation and Expression of Differentiation–Specific α–Smooth Muscle Actin in Arterial Smooth Muscle Cells", 1989, J. Exp. Med., 170:1595–608.
Higashiyama, S., et al., "Heparin–binding EGF–Like Growth Factor Stimulation of Smooth Muscle Cell Migration: Dependence on Interactions with Cell Surface Heparan Sulfate", 1993, J. Cell Biology, 122(4):933–40.
Higashiyama, S., et al., "Structure of Heparin–binding EGF–Like Growth Factor", 1992, J. Biol. Chem., 267(9):6205–12.

Nigashiyama, S., et al., "A Heparin–binding Growth Factor Secreted by Macrophage–Like Cells That is Related to EGF", 1991, Science,251:936–39.
Itoh, H., et al., "Atrial Natriuretic Polypeptide Inhibits Hypertrophy of Vascular Smooth Muscle Cells", 1990, J. Clin. Invest., 86:1690–97.
Jahroudi, N., et al., "Endothelial–Cell–Specific Regulation of von Willebrand Factor Gene Expression", 1994, Molecul. and Cellular Biol., 14(2):999–1008.
Lee, M.E., et al., "Functional Analysis of the Endothelin–1 Gene Promoter", 1990, J. Biol. Chem., 265(18):10446–50.
Lee, M.E., et al., "Cloning of the GATA–binding Protein That Regulates Endothelin–1 Gene Expression in Endothelial Cells", 1991, J. Biol. Chem., 266(24):16188–92.
Lee, M.E., et al., "Regulation of Endothelin–1 Gene Expression by Fos and Jun", J. Biol. Chem., 266(28):19034–39.
Luo, Y., et al., "A Novel B Cell–Derived Coactivator Potentiates the Activation of Immunoglobulin Promoters by Octamer–Binding Transcription Factors", 992, Cell, 71:231–41.
Maxm, A.M., et al., "A New Method for Sequencing DNA", 1977, Proc. Natl. Acad. Sci. USA, 74(2):560–64.
Melani, C., et al., "Inhibition of Proliferation by c–myb Antisense Oligodeoxynucleotides in Colon Adenocarcinoma Cell Lines that Express c–mby[1]", 1991, Cancer Res., 51:2897–901.
Nakano, T., et al, "Glucocorticoid Inhibits Thrombin–induced Expression of Platelet–derived Growth Factor A–chain and Heparin–binding Epidermal Growth Factor–Like Growth Factor in Human Aortic Smooth Muscle Cells", 1993, J. Biol. Chem., 268(30):22941–47.
Orkin, S.H., "GATA–Binding Transcription Factors in Hematopoietic Cells", 1992, Blood, 80(3):575–81.
Osborn, L., et al., "Tumor Necrosis Factor α and Interleukin 1 Stimulate the Human Immunodeficiency Virus Enhancer by Activation of the Nuclear kB", 1989, Proc. Natl., Acad. Sci. USA, 86:2336–40.
Ravid, K., et al., "Transcriptional Regulation of the Rat Platelet Factor 4 Gene: Interaction Between an Enhancer/Silencer Domain and the GATA Site", 1991, Molec. and Cellular Biol., 11(12):6116–27.
Ross, R., "The Pthogenesis of Atherosclerosis: A Perspective for the 1990s", 1993, Nature, 362:801–809.
Schwartz, S.M., et al., "Developmental Mechanisms Underlying Pathology of Arteries", 1990, Physiological Revs., 70(4):1177–209.
Springer, T.A., "Adhesion Receptors of the Immune System", 1990, Nature, 346:425–34.

(List continued on next page.)

Primary Examiner—Marianne P. Allen
Attorney, Agent, or Firm—Fish & Richardson P.C.

[57] ABSTRACT

A substantially pure DNA comprising an endothelial cell-specific enhancer for expression of heterologous polypeptides and antisense nucleic acid sequences in endothelial cells for the purpose of treating arteriosclerosis.

20 Claims, 4 Drawing Sheets

OTHER PUBLICATIONS

Temizer, D.H., et al., "Induction of Heparin–binding Epidermal Growth Factor–Like Growth Factor mRNA by Phorbol Ester and Angiotensin II in Rat Aortic Smooth Muscle Cells", 1992, *J. Biol. Chem.*, 267(34):24892–96.

Wilson, D.B., et al., "A Nonerythroid GATA–Binding Protein is Required for Function of the Human Preproendothelin–1 Promoter in Endothelial Cells", 1990, *Molec. and Cellular Biol.*, 10(9):4854–62.

Yoshizumi, et al., "Tumor Necrosis Factor Increases Transcription of the Heparin–binding Epidermal Growth Factor–like Growth Factor Gene in Vascular Endothelial Cells", 1992, *J. Biol. Chem.*, 267(14):9467–69.

yu, K.,et al., "Transcriptional Regulation of the Thrombomodulin Gene", 1992, *J. Biol. Chem.*, 267(32):23237–47.

Fen, Z et al., "Structural Organization and Chromosomal Assignment of the Gene Encoding the Human Heparin Binding Epidermal Growth Factor–like Growth Factor/ Diphtheria Toxin Receptor". 1993, *Biochem.*, 32:7932–38.

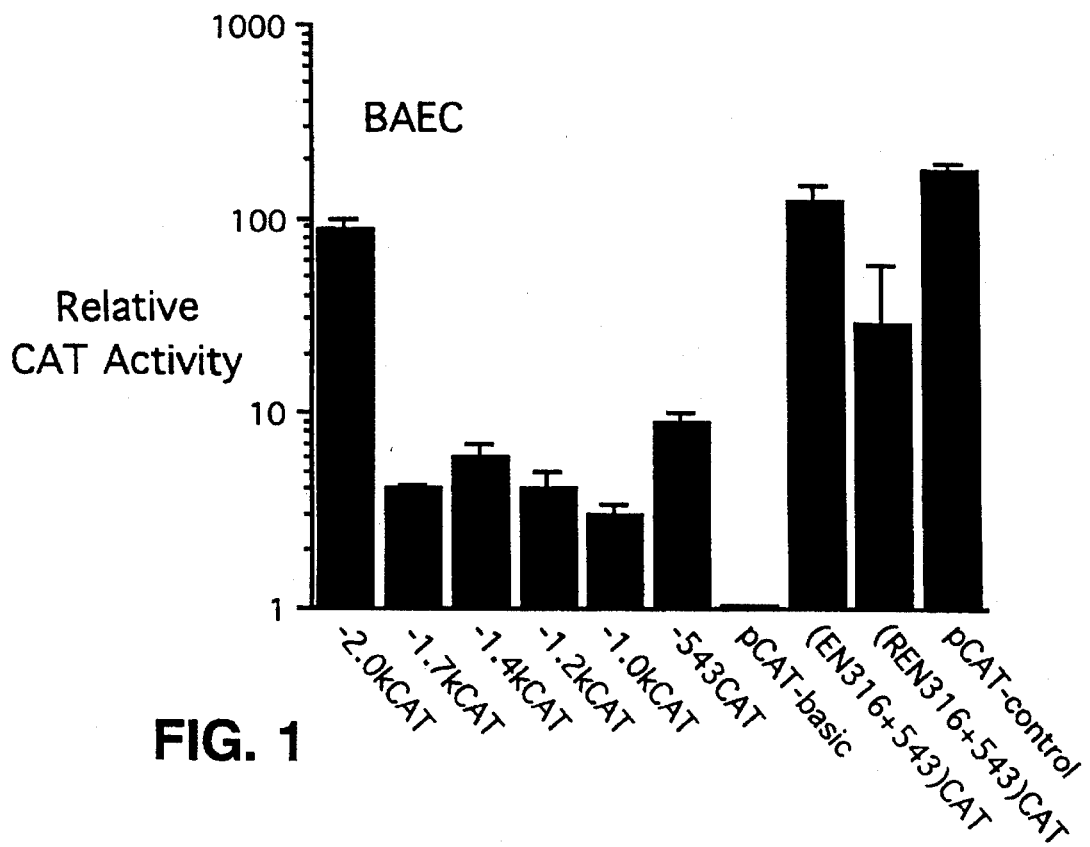

FIG. 1

```
TTTATCTTCTTTTTTTCAGGCCCTTCCTGTAAAACCTGGCT  -1962
                        ‡
GACACACAAACCTAGCTGGGGTGAGGCTCCAGGTGTGATG  -1922

AAAGTTTGGAGTTGCCCCATGAATGGGACTGAGGCTGATG  -1882
      EnII
TGGGGGTGAGAAGGCGGAAGGACAGAGCATGTGAAGGGAG  -1842
                 ↓
AAAGGCAGGCTGGGGCAAGAGAGCAGGGTGTGACTCTGGC  -1802
          EnI
GAGGGTGGGGGAAAGGGGGTGATTTGACCATGTGTCAGGA  -1762

AGTGTTTCTCTCCACCCTCCCCTGGGGAGAGCCTTGACCC  -1722

CAAGGTGGCTTTGTTTTGGGGAAGCAGGTGGCCAGG     -1686
```

FIG. 2

ENDOTHELIAL CELL-SPECIFIC ENHANCER

BACKGROUND OF THE INVENTION

The field of the invention is cell-specific expression of proteins.

Heparin-binding epidermal growth factor-like growth factor (HB-EGF) is a 22-kDa protein originally purified from the conditioned medium of macrophage-like U-937 cells. The human gene encoding HB-EGF has been cloned (Fen et al., 1993, Biochemistry 32:7932–7938), and is organized into six exons spanning approximately 14 kb. The mature processed peptide contains at least 86 amino acids and is a potent mitogen and chemoattractant for vascular smooth muscle cells but not endothelial cells (Higashiyama et al., 1992, J. Biol. Chem. 267:6205–6212; Higashiyama et al., 1993, J. Cell Biol. 122:933–940). Expression of HB-EGF is regulated by cytokines in vascular endothelial cells (Yoshizumi et al., 1992, J. Biol. Chem. 267:9467–9469) and by phorbol esters, angiotensin II, and thrombin in vascular smooth muscle cells (Temizer et al., 1992, J. Biol. Chem. 267:24892–24896; Dluz et al., 1993, J. Biol. Chem. 268:18330–18334; Nakano et al., 1993, J. Biol. Chem. 268: 22941–22947). HB-EGF also appears to be transcribed and regulated in cultured cells commonly associated with atherosclerotic lesions (Ross, R., 1993, Nature 362:801–809; Schwartz et al., 1990, Physiol. Rev. 70:1177–1209), but the molecular mechanisms regulating transcription of this gene have not been defined.

SUMMARY OF THE INVENTION

The inventors have now discovered the molecular basis of endothelial cell-specific gene transcription and disclose DNA sequences containing an endothelial cell-specific enhancer. The invention features a substantially pure DNA which includes a heparin-binding epidermal growth factor-like growth factor (HB-EGF) enhancer. The DNA preferably does not encode HB-EGF.

A "substantially pure DNA" as used herein refers to a DNA which has been purified from the sequences which flank it in a naturally occurring state, i.e., a DNA fragment which has been removed from the sequences which are normally adjacent to the fragment, e.g., the sequences adjacent to the fragment in the genome in which it naturally occurs, and which has been substantially purified from other components which naturally accompany the DNA, e.g., DNA which has been purified from the proteins which naturally accompany it in the cell.

The claimed HB-EGF enhancer may contain a nucleotide sequence substantially identical to SEQ ID NO:1. Alternatively, the DNA of the invention may contain a nucleotide sequence substantially identical to SEQ ID NO:2, a nucleotide sequence substantially identical to SEQ ID NO:3, or a nucleotide sequence containing sequences substantially identical to both SEQ ID NO:2 and SEQ ID NO:3.

A substantially identical DNA is preferably at least 50%, more preferably at least 85%, more preferably at least 90%, and most preferably at least 95% identical to a reference nucleic acid sequence.

The DNA of the invention may contain the claimed HB-EGF enhancer and a DNA sequence encoding a heterologous polypeptide operably linked to regulatory sequences, e.g., a promoter, for expression of the polypeptide. According to the invention, the HB-EGF enhancer is located sufficiently close to the heterologous polypeptide-encoding DNA to upregulate the level of transcription thereof. The enhancer may be in a position immediately adjacent to the transcriptional start site of the heterologous polypeptide-encoding DNA or up to several kilobases upstream or downstream of the transcriptional start site. A "heterologous polypeptide" is herein defined as any polypeptide other than HB-EGF. The heterologous polypeptide may be for example, a thrombolytic agent, e.g., a plasminogen activator such as tissue-type plasminogen activator, urokinase, prourokinase, streptokinase, or staphylokinase. The heterologous polypeptide may alternatively be a polypeptide that inhibits the proliferation of smooth muscle cells, e.g., interferon-γ, an atrial natriuretic polypeptide. DNA containing the HB-EGF enhancer of the invention and a DNA sequence encoding a heterologous polypeptide can be administered to animals to treat vascular diseases, such as arteriosclerosis, hypertension, and excessive blood clotting.

Also within the invention is a vector containing the HB-EGF enhancer of the invention and a DNA encoding a heterologous peptide operably linked to regulatory sequences. The invention also includes a cell containing such a vector. The cell is preferably an endothelial cell. The vector of the invention may be introduced into an endothelial cell to direct endothelial cell-specific expression of the heterologous peptide.

The DNA of the invention may also contain the HB-EGF enhancer of the invention and a DNA sequence which is transcribed into an RNA which is complementary, i.e., antisense, to a naturally occurring mRNA. The HB-EGF enhancer is located sufficiently close to the DNA sequence to be transcribed to upregulate the level of its transcription. Following transcription of the DNA into antisense RNA, the antisense RNA binds to its target mRNA molecule within a cell, thereby inhibiting translation of the target mRNA and down-regulating expression of the protein or polypeptide encoded by the target mRNA. If, for example, the gene product of the target sequence stimulates proliferation of smooth muscle cells, down-regulation of gene expression after antisense binding will result in suppression of smooth muscle cell proliferation.

The invention features a method of inhibiting arteriosclerosis in an animal by contacting an artery of the animal with a DNA containing the claimed HB-EGF enhancer and a DNA sequence which is transcribed into an antisense RNA which is complementary to the mRNA of a protein involved in the development of arteriosclerosis, e.g., HB-EGF. Since HB-EGF acts as a mitogen for smooth muscle cells, inhibition of HB-EGF expression would result in a decrease in the proliferation of smooth muscle cells and a concomitant reduction in arteriosclerosis. Expression of cell surface adhesion molecules, e.g., endothelial leukocyte adhesion molecule, intercellular adhesion molecule or vascular cell adhesion molecule, has also been associated with the development of arteriosclerosis. Accordingly, the methods of the invention can be used to downregulate the expression of such proteins or polypeptides by utilizing DNA constructs which contain the HB-EGF enhancer of the invention and a DNA sequence which is transcribed into an antisense RNA which is complementary to the mRNA of an adhesion molecule.

The invention also provides a method of inhibiting arteriosclerosis by contacting an artery with a compound which binds to all or part of the HB-EGF enhancer, e.g., SEQ ID NO:1, SEQ ID NO:2, SEQ ID NO:3, or both SEQ ID NO:2 and SEQ ID NO:3. Binding of a compound to some or all of the HB-EGF enhancer would prevent a cellular trans-acting element, e.g., an endothelial cell-specific nuclear factor, from binding to the enhancer DNA. A decrease in the binding of such an endothelial cell-specific trans-acting element to the enhancer DNA would result in the prevention or reduction of HB-EGF expression, resulting in a decrease in arterial smooth muscle cell proliferation.

The invention also provides methods of screening for compounds which bind to some or all of the HB-EGF enhancer and/or block the interaction of a trans-acting factor with the enhancer DNA. The screening assay may be carried out by contacting a candidate compound with DNA containing SEQ ID NO:1 and determining whether the compound binds to the DNA. Alternatively, DNA containing SEQ ID NO:2, SEQ ID NO:3, or both, may be used to contact the candidate compound. Binding of the compound to enhancer DNA correlates with the ability of the compound to inhibit expression of HB-EGF. A compound which inhibits HB-EGF expression may also be identified by (a) contacting a candidate compound with HB-EGF enhancer-containing DNA, e.g., DNA containing SEQ ID NO:1, SEQ ID NO:2, SEQ ID NO:3, or SEQ ID NO:2 and SEQ ID NO:3, (b) contacting the compound with an endothelial cell-specific polypeptide, e.g., a trans-acting nuclear factor, [steps (a) and (b) may be carried out in any order, i.e., they are interchangeable], and (c) determining the level of binding of the polypeptide to the enhancer DNA. A decrease in the level of binding of the endothelial cell-specific polypeptide in the presence of the compound compared to the level in the absence of the compound indicates that the compound inhibits the expression of HB-EGF.

Other features and advantages of the invention will be apparent from the following description of the preferred embodiments thereof, and from the claims.

DETAILED DESCRIPTION

The drawings will first be described.

FIG. 1 is a bar graph showing the results of a functional analysis of the human HB-EGF enhancer/promoter region by transfection of chloramphenicol acetyltransferase (CAT) reporter gene constructs. A series of deletion mutants containing various fragments of the HB-EGF 5' flanking sequence and the reporter gene CAT (plasmids −2.0kCAT, −1.7kCAT, −1.4kCAT, −1.2kCAT, −1.0kCAT, and −543CAT containing approximately 2.0 kb, 1.7 kb, 1.4 kb, 1.2 kb, 1.0 kb, and 543 nucleotides of HB-EGF 5' flanking sequence, respectively) were transfected into bovine aortic endothelial cells (BAEC). "+1" refers to the first nucleotide of the HB-EGF transcriptional start site, and "−1" refers to the first non-transcribed nucleotide 5' to the HB-EGF transcriptional start site. Plasmid pCAT-basic contained no promoter and plasmid pCAT-control contained the SV40 enhancer and promoter. A 316-bp HindIII-PvuII fragment corresponding to nucleotides −2001 to −1686 of the HB-EGF gene (SEQ ID NO:1), termed enhancer (EN) region 316, was cloned (in both orientations) into plasmid −543CAT 5' to the HB-EGF genomic fragment to generate the plasmid (EN316+543)CAT and the reverse plasmid (REN316+543)CAT. For each CAT construct, plasmid pSVβGAL was cotransfected to correct for differences in transfection efficiency. CAT activity and β-galactosidase activity were measured, and relative CAT units were calculated. The y axis is in log scale.

FIG. 2 is a diagram of the nucleotide sequence of enhancer (EN) region 316 (SEQ ID NO:1). EN316 was sequenced from both ends by the dideoxy chain termination method known in the art. The atypical GATA motif (TTATCT) is indicated with boldface type. The two protected regions identified by DNase I footprinting analysis, EnI (SEQ ID NO:2) and EnII (SEQ ID NO:3), are underlined. The first nucleotide of DNA fragments EN249 and EN140 is designated by ‡ and ↓, respectively.

Figure 3:
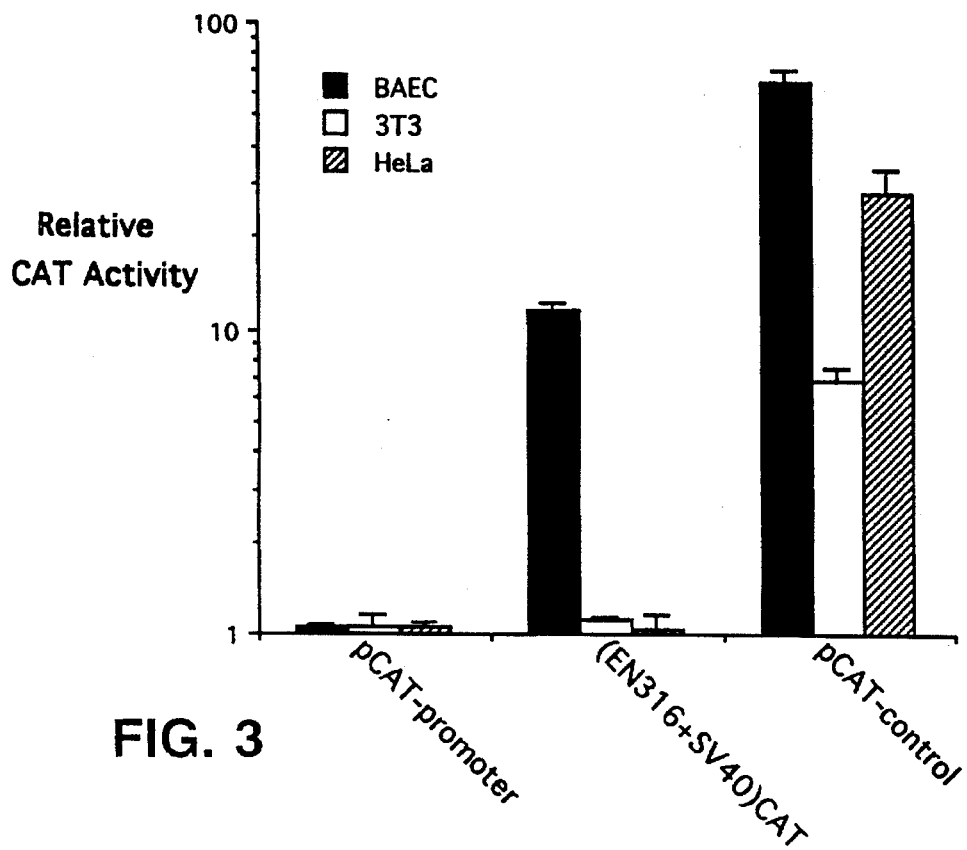

FIG. 3 is a bar graph showing that EN316 (SEQ ID NO:1) confers activity to a heterologous promoter in BAEC but not in HeLa or 3T3 cells. To determine whether EN316 increased the activity of a heterologous promoter, EN316 was cloned upstream of the minimal SV40 promoter in the pCAT-promoter and the plasmids were transfected into BAEC, 3T3 cells (a mouse fibroblast cell line), and HeLa cells (a human epidermoid carcinoma cell line). Plasmid pCAT-control contained the SV40 enhancer and promoter. The y axis is in log scale.

Figure 4:
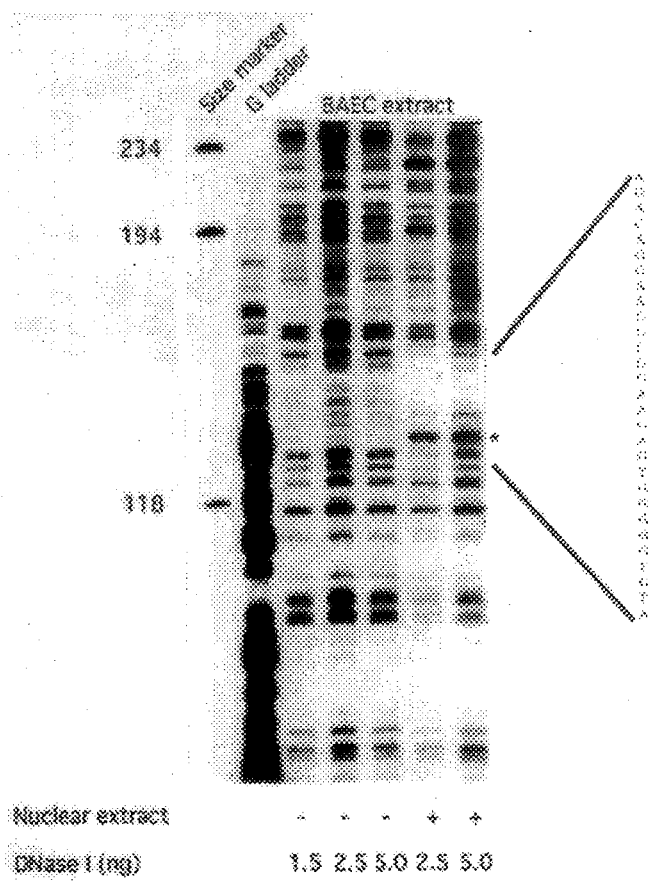

FIG. 4 is a photograph of a DNase I footprinting analysis showing a characterization of the protein-binding motif in the HB-EGF enhancer region. EN316 (SEQ ID NO:1) was labeled at the 5' end of the sense strand and 10,000 cpm of the probe was incubated in the presence (+) or absence (−) of BAEC nuclear extract containing 20 µg of protein for 15 min at 0° C. The reaction mixture was then treated with various concentrations of DNase I (as indicated) at 22° C. for 2 min. Reaction products were separated on a 6% sequencing gel and analyzed by autoradiography. The size marker (in bp) was prepared by radiolabeling φX174RF DNA digested with HaeIII, and the G sequence pattern (G ladder) of EN316 was generated by the well-known Maxam and Gilbert technique. The DNA sequence corresponding to the EnII (SEQ ID NO:3) protected region is shown to the right of the DNA footprint. The asterisk indicates DNase I-hypersensitive sites induced by binding of nuclear protein.

Figure 5A:
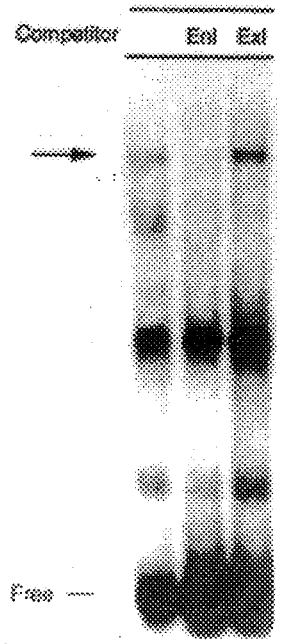

FIG. 5A is a photograph of a competition assay showing binding of nuclear proteins to EnI (SEQ ID NO:2). Electrophoretic mobility shift analysis (EMSA) was performed with a $^{32}$P-labeled DNA fragment encoding EnI. Addition of BAEC nuclear extract resulted in a shifted band, as indicated by the arrow.

Figure 5B:
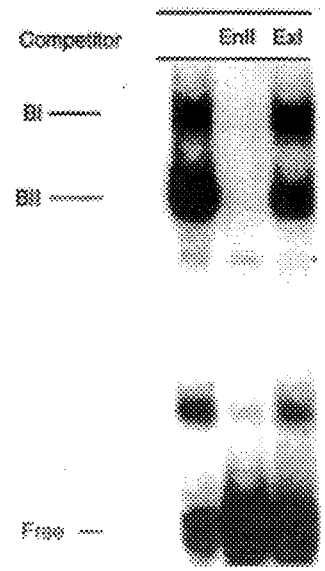

FIG. 5B is a photograph of a competition assay showing binding of nuclear proteins to EnII (SEQ ID NO:3). EMSA was performed with a $^{32}$P-labeled DNA fragment encoding EnII. Addition of BAEC nuclear extract resulted in a shifted band, as indicated by BI and BII.

Figure 6:
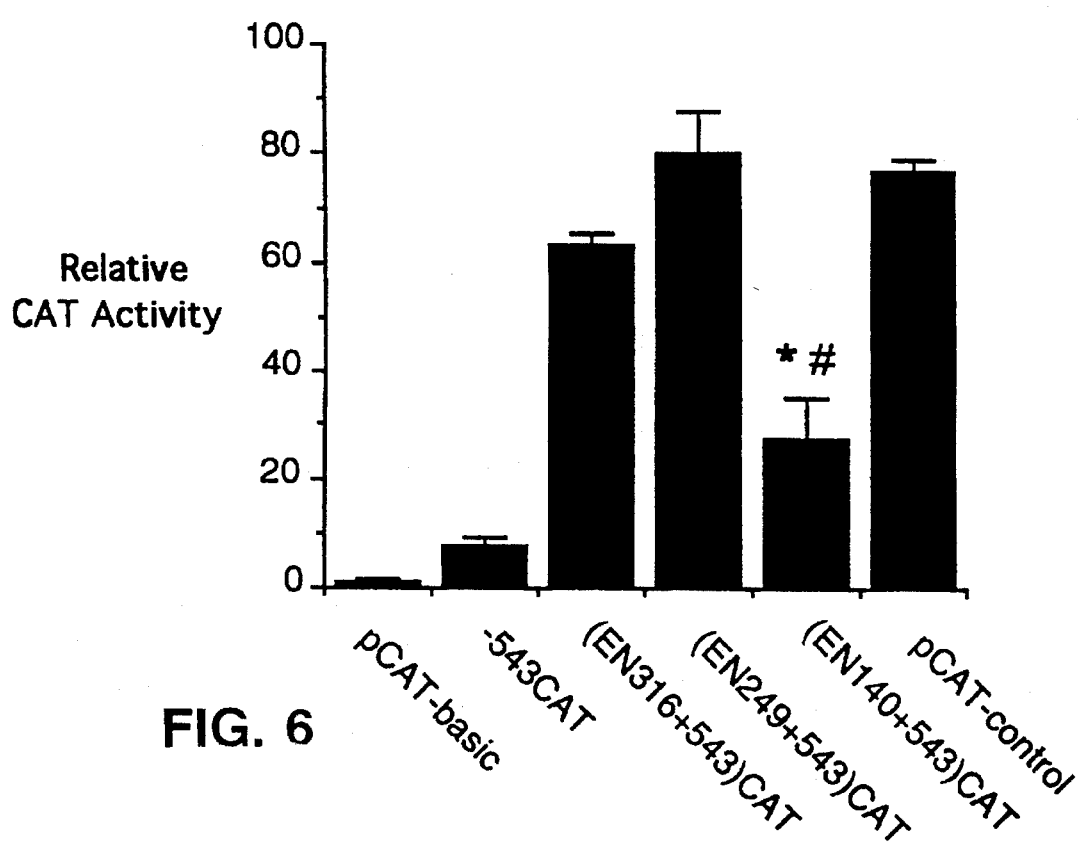

FIG. 6 is a bar graph showing that the GATA motif in EN316 (SEQ ID NO:1) is inactive. Two DNA fragments, EN249 and EN140 (corresponding to nucleotides −1934 to −1686 and nucleotides −1825 to −1686 of the human HB-EGF gene, respectively) were cloned into −543CAT to generate plasmids (EN249+543)CAT and (EN140+543) CAT, which were then transfected into BAEC. EN249 contained EnI (SEQ ID NO:2) and EnII (SEQ ID NO:3) and excluded the GATA site; EN140 contained only EnI (and excluded the GATA site). *p<0.05, (EN140+543)CAT versus (EN249+543)CAT; #p<0.05, (EN140+543)CAT versus −543CAT.

Figure 7:
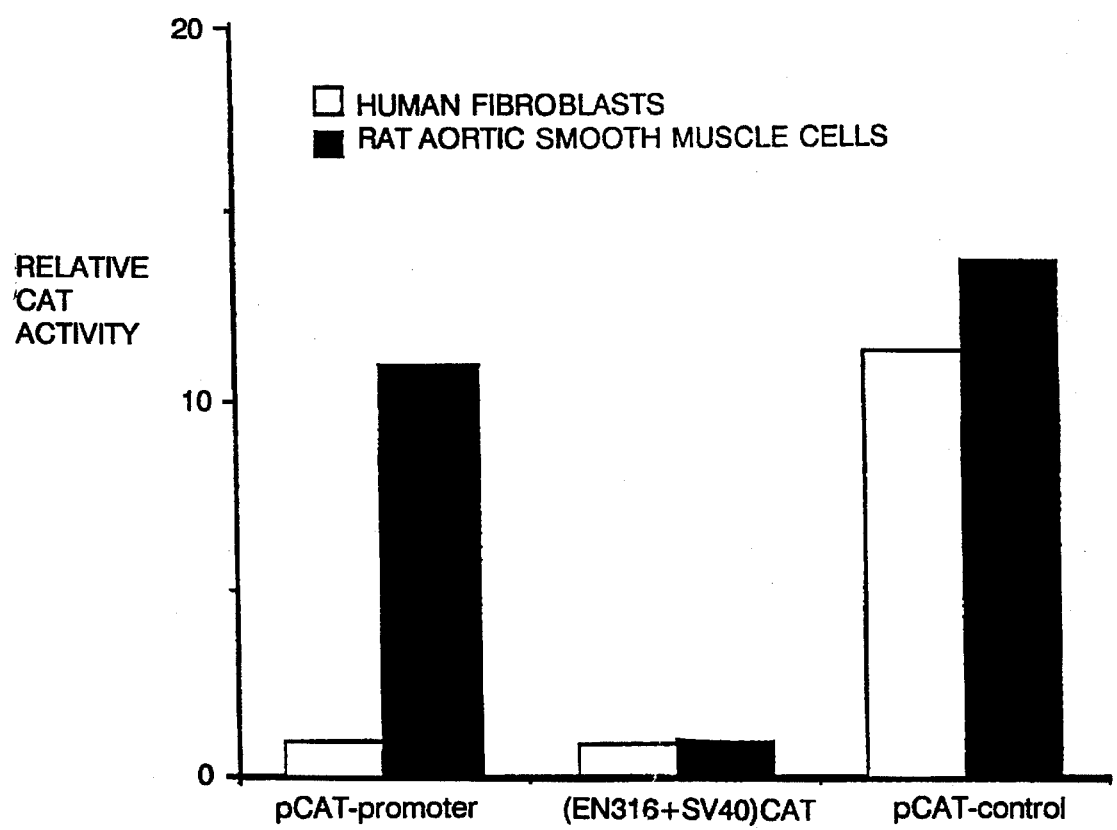

FIG. 7 is a bar graph showing the cell-specific enhancer activity of EN316 (SEQ ID NO:1). Plasmids pCAT-promoter, (EN316+SV40)CAT, and pCAT-control were transfected into human fibroblasts (white bars) and rat aortic smooth muscle cells (black bars). Although the SV40 enhancer, which is not cell type-specific, increased promoter activity in these two cell types, EN316 failed to increase the activity of the heterologous promoter in human fibroblasts and rat aortic smooth muscle cells.

Cell Culture and Nuclear Extracts

BAEC were isolated and cultured in Dulbecco's modified Eagle's medium supplemented with 10% fetal calf serum (Hyclone), 600 μg of glutamine/ml, 100 units of penicillin/ml, and 100 μg of streptomycin/ml. The cells were passaged every 3-5 days. Cells from passages 4-7 were used for transfection experiments and for the preparation of nuclear extract. HeLa cells and 3T3 cells (American Type Culture Collection #CCL2 and CCL92, respectively were cultured under conditions identical to those for BAEC. Nuclear extracts from BAEC, HeLa cells, and 3T3 cells were prepared using methods known in the art.

Plasmids

All reporter plasmids contained the prokaryotic CAT gene (Promega, Madison, Wis.) in conjunction with (a) the cloned HB-EGF 5' promoter sequence, (b) synthetic complementary oligonucleotides encoding a portion of the HB-EGF 5' sequence, or (c) the SV40 enhancer/promoter sequence. The plasmid pCAT-basic contained no promoter; pCAT-promoter contained the minimal SV40 promoter; and pCAT-control contained the SV40 promoter and enhancer. The plasmid pSVβGAL (Promega, Madison, Wis.) contained the β-galactosidase gene driven by the SV40 promoter and enhancer.

A DNA fragment containing 2.0 kb of 5' flanking region from the HB-EGF gene and 70 nucleotides of its first exon was cloned into the pCAT-basic plasmid to generate the plasmid -2.0kCAT. Then the 2.0-kb HB-EGF 5' flanking sequence in -2.0kCAT was digested with restriction enzyme or exonuclease III from the 5' end to generate a series of truncated fragments containing approximately 1.7 kb, 1.4 kb, 1.2 kb, 1.0 kb, and 543 nucleotides of the HB-EGF 5' flanking sequence. These truncated DNA fragments were cloned into pCAT-basic in the 5' to 3' orientation to generate the plasmids -1.7kCAT, -1.4kCAT, -1.2kCAT, -1.0kCAT, and -543CAT. A 316-bp HindIII-PvuII fragment corresponding to nucleotides -2001 to -1686 (SEQ ID NO:1) of the HB-EGF gene, termed EN316, was cloned (in both orientations) into plasmid -543CAT 5' of the HB-EGF genomic fragment to generate the plasmid (EN316+543)CAT and the reverse plasmid (REN316+543)CAT. EN316 was also cloned 5' of the minimal SV40 promoter in pCAT-promoter to generate the plasmid (EN316+SV40) CAT. Two HB-EGF DNA fragments corresponding to nucleotides -1934 to -1686 [EN249, spanning EnI (SEQ ID NO:2) and EnII (SEQ ID NO:3) and excluding the GATA site] and nucleotides -1825 to -1686 [EN140, spanning EnI (SEQ ID NO:2) only and excluding the GATA site] were amplified by polymerase chain reaction and cloned into plasmid -543CAT to generate the plasmids (EN249+543) CAT and (EN140+543)CAT, respectively.

Transfection and CAT Assays

BAEC were transfected with 20 mg of the appropriate CAT construct by the calcium phosphate method known in the art. To correct for variability in transfection efficiency, 5 μg of pSVβGAL plasmid DNA was cotransfected in all experiments. Cell extracts were prepared 48 hours after transfection. The CAT assay was performed by a modified two-phase fluor diffusion method. A reaction mixture containing [$^{14}$C]acetyl coenzyme A (NEC-313L, 4.0 mCi/mmol, DuPont) and 1M Tris-HCl (pH 7.8) was added to the cell extract to achieve a final concentration of 1.0 mM chloramphenicol, 0.1 mM [$^{14}$C]acetyl coenzyme A, and 100 mM Tris-HCl. The reaction mixture was gently overlaid with 5 ml of a water-immiscible scintillation fluor (Econofluor, DuPont) and then incubated at 37° C. for 2 h. Scintillation assays were performed in a Beckman counter.

β-Galactosidase activity was determined and the ratio of CAT activity to β-galactosidase activity in each sample was used as a measure of normalized CAT activity. The normalized CAT activity in each sample was divided by that of pCAT-basic or pCAT-promoter and expressed as relative CAT activity. Each construct was transfected at least three times, and each transfection was done in duplicate. Data for each construct are presented as the mean ±SEM. Comparisons among constructs of normalized CAT activity were performed by applying a factorial analysis of variance followed by Fisher's least significant difference test. Statistical significance was accepted at $p<0.05$.

DNase I Footprinting

DNA fragment EN316 (SEQ ID NO:1) was labeled at either end with [$\alpha$-$^{32}$P]dCTP by using the Klenow fragment of DNA polymerase I. About 10,000 cpm (10 pg) of labeled DNA fragment was incubated with BAEC nuclear extract and 1 μg of poly(dI.dC).poly(dI.dC) on ice for 20 min and then 2 min at room temperature. Samples were treated with DNase I (1.5, 2.5, and 5.0 ng for samples with and without nuclear extract) for 2 min at 22° C. Samples were then extracted with phenol/chloroform, precipitated in ethanol, and analyzed by electrophoresis on an 8% polyacrylamide/urea gel. A G ladder of the same end-labeled DNA fragment was generated by the Maxam and Gilbert technique known in the art.

EMSA

EMSA was performed with probes made from annealed oligonucleotides encoding a portion of the HB-EGF gene. The oligonucleotides were labeled with [$\gamma$-$^{32}$P]ATP by using polynucleotide kinase before annealing. A typical binding reaction mixture contained 20,000 cpm of DNA probe, 1 μg of bovine serum albumin, 5 μg of BAEC nuclear extract, and 0.2 μg of ploy(dI.dC).poly(dI.dC) for EnI (SEQ ID NO:2) or 2 μg of poly (dG.dC).poly(dG.dC) for EnII (SEQ ID NO:3). The samples were incubated at 0° C. for 40 min and analyzed on 4% native polyacrylamide gels in a TBE buffer (12.5 mM Tris, 12.25 mM boric acid, and 0.25 mM EDTA). Binding specificity was measured by competition with a 100-fold molar excess of unlabeled oligonucleotide ExI, which codes for a sequence in the first exon of the human HB-EGF gene (TTCTTGAGTGTCTTGTCTTGCTCACTCAGCCC) (SEQ ID NO:4).

Promoter and Enhancer Activity of the 5' Flanking Sequence of the HB-EGF Gene

The CAT activity induced by plasmid -2.0kCAT in BAEC was about 100 times higher than that induced by the promoterless pCAT-basic (FIG. 1) and similar to that induced by pCAT-control, which is driven by the potent SV40 enhancer and promoter. A plasmid containing 8.6 kb of HB-EGF 5' flanking sequence in pCAT-basic was found to induce CAT activity similar to that of -2.0kCAT. These data indicate that the 2.0-kb 5' flanking region of the HB-EGF gene contains high promoter and enhancer activity.

To further localize the positive regulatory elements directing HB-EGF gene expression, BAEC was transfected with a series of deletion mutants generated by restriction enzyme and exonuclease III digestion. In comparison with plasmid -2.0kCAT, plasmid -1.7kCAT (containing 1686 nucleotides of HB-EGF 5' flanking sequence) was associated with a greater than tenfold reduction in CAT activity, suggesting the existence of a positive regulatory element between nucleotide -2001 and -1686 (SEQ ID NO:1) of the HB-EGF 5' flanking sequence. The plasmids in which the HB-EGF 5' flanking sequence had been reduced further, -1.4kCAT, -1.2kCAT, -1.0kCAT, and -543CAT, produced no additional reduction in CAT activity (FIG. 1). The activity of -543CAT (containing only 543 nucleotides of HB-EGF 5' flanking sequence) was nine times higher than that of the promoterless pCAT-basic.

To determine whether the 316-nucleotide DNA fragment between nucleotide −2001 and −1686 (EN316; SEQ ID NO:1) contained enhancer activity, EN316 was cloned upstream of −543CAT in the appropriate orientation to produce (EN316+543)CAT and in the reverse orientation to produce (REN316+543)CAT. In both orientations, this DNA fragment significantly increased CAT activity in comparison with that of the parent −543CAT (FIG. 1). When cloned in the correct orientation, EN316 increased the activity of −543CAT to a level similar to that of −2.0kCAT (FIG. 1, (EN316+543)CAT versus −2.0kCAT).

The data in FIG. 1 indicate the presence of potent enhancer activity between nucleotide −2001 and −1686 (SEQ ID NO:1) and promoter activity between nucleotide −543 and +70. To determine whether EN316 contained any known positive regulatory elements, the DNA fragment containing the EN316 region (SEQ ID NO:1) was sequenced from both ends (FIG. 2). The nucleotide sequence of EN316 revealed no known motifs, with the exception of an atypical GATA consensus sequence between nucleotides −2000 to −1995 (FIG. 2, TTATCT). The classic GATA motif with the consensus sequence, ((A/T)GATA(A/G)), and its cognate binding protein, GATA-2, have been shown to be important for gene expression in vascular endothelial cells (Dorfman et al., 1992, J. Biol. Chem. 267:1279–1285; Lee et al., 1991, J. Biol. Chem. 266:16188–16192; Orkin, S. H., 1992), Blood 80:575–581).

Evidence of an Endothelial Cell-specific Enhancer Sequence

To determine whether the HB-EGF enhancer elements within EN316 (SEQ ID NO:1) were cell type-specific, a fusion plasmid, (EN316+SV40)CAT, in which EN316 was cloned 5' of the minimal SV40 promoter in pCAT-promoter (Promega, Madison, Wis.) and which lacked enhancer elements, was constructed. pCAT-promoter, (EN316+SV40) CAT, and pCAT-control were then transfected into BAEC, 3T3 cells (mouse fibroblast cells) and HeLa cells (human epidermoid carcinoma cells). In comparison with plasmid pCAT-promoter, plasmid (EN316+SV40)CAT was associated with a more than tenfold increase in CAT activity in BAEC but not in other cell types (FIG. 3). In contrast, plasmid pCAT-control (containing the universal SV40 enhancer) increased CAT activity in all cell types. These data indicate that EN316, encoding nucleotides −2001 to −1686 (SEQ ID NO:1) of the human HB-EGF gene, contains a potent, endothelial cell-specific cis-acting element that enhances the activity of both homologous and heterologous promoters and that there is promoter activity between nucleotides −543 and +70 (FIG. 1). The promoter is not cell-type specific, as it is active in BAEC (FIG. 1) as well as 3T3 cells and HeLa cells. However, the enhancer was found to be endothelial cell-specific since the −2001 to −1686 sequence (EN316; SEQ ID NO:1)) conferred enhancer activity to a heterologous promoter in endothelial cells but not 3T3 cells or HeLa cells (FIG. 3).

Characterization of the Protein-binding Motif in the HB-EGF Enhancer

DNase I footprinting analyses were carried out to characterize the protein binding motif in EN316 (SEQ ID NO:1). The EN316 DNA fragment was labeled at the 5' end of the sense strand and was incubated in the presence (+) or absence (−) of BAEC nuclear extract containing 20 µg of protein for 15 min at 0° C. The reaction mixture was then treated with various doses of DNase I (as indicated in FIG. 4) and the reaction products were separated on a 6% sequencing gel and analyzed by autoradiography. Incubation of the DNA fragment with BAEC extract revealed two protected regions spanning nucleotides −1884 to −1856 (EnII; SEQ ID NO:3) (FIGS. 2 and 4) and nucleotides −1789 to −1776 (EnI; SEQ ID NO:2) (FIG. 2) of the human HB-EGF gene. These results were confirmed using the same DNA fragment labeled at the antisense strand. EnI (SEQ ID NO:2) and EnII (SEQ ID NO:3) were found to share an identical sequence, GGGGGTGA (FIG. 2). A comparison of this sequence with transcriptional factor motifs in the GenBank data base revealed no similar sequences (Ghosh, D., 1992, Nucl. Acid Res. 20S:2091–2093).

To determine whether EnI (SEQ ID NO:2) and EnII (SEQ ID NO:3) bound nuclear proteins, EMSA was performed with labeled DNA fragments synthesized according to the sequences of EnI and EnII (FIG. 2). Incubation of labeled EnI probe with nuclear extract prepared from BAEC retarded the mobility of EnI and resulted in the formation of the band indicated by the arrow in FIG. 5A. This band was specific because a 100-fold molar excess of unlabeled oligonucleotide encoding EnI (SEQ ID NO:2), but not that encoding the unrelated oligonucleotide ExI (SEQ ID NO:4), competed for protein binding. Unlabeled EnII oligonucleotide, which shares a common GGGGGTGA sequence, also blocked binding. Incubation of labeled EnII probe with BAEC nuclear extract resulted in the formation of two specific bands, BI and BII (FIG. 5B). Unlabeled EnI blocked the formation of BII but not BI. These data indicate that EnI (SEQ ID NO:2) and EnII (SEQ ID NO:3) both bind nuclear protein.

Inactive GATA Site in Enhancer Region 316

DNase I footprinting did not show protein binding to the GATA site within EN316 (SEQ ID NO:1). To completely eliminate the possibility that the GATA site was functional, two DNA fragments, EN249 (encoding nucleotides −1934 to −1686) and EN140 (encoding nucleotides −1825 to −1686), were generated using EN316 as template. EN249 contained EnI (SEQ ID NO:2) and EnII (SEQ ID NO:3) and excluded the GATA site; EN140 contained only EnI (SEQ ID NO:2) (and excluded the GATA site). EN249 and EN140 were cloned into −543CAT to generate the plasmids (EN249+543)CAT and (EN140+543)CAT, which were then transfected into BAEC (FIG. 6). (EN316+543)CAT and (EN249+543)CAT both increased the activity of −543CAT to a similar level, indicating that the GATA site was not important. In contrast, the enhancer activity of (EN140+543)CAT decreased markedly in comparison with that of (EN249+543)CAT, suggesting that EnII may be functionally important. However, the CAT activity induced by plasmid (EN140+543)CAT was significantly higher than that induced by −543CAT. This data suggests the presence of enhancer activity in EN140, which contains EnI (SEQ ID NO:2) only.

The GATA site has been implicated in mediating the cell-type specific expression of genes such as those for platelet factor 4, thrombomodulin, and von Willebrand factor (Ravid et al., 1991, Mol. Cell Biol. 11:6116–6127; Yu et al., 1992, J. Biol. Chem. 267: 23237–23247; Jahroudi et al., 1994, Mol. Cell Biol. 14:999–1008). In addition, GATA sites in conjunction with AP1 sites are important in directing high-level endothelin-1 gene expression in endothelial cells (Lee et al., 1990, J. Biol. Chem. 265:10446–10450; Lee et al., 1991, J. Biol. Chem. 266:19034–19039; Dorfman et al., supra; Lee et al., 1991, J. Biol. Chem. 266:16188–16192; Wilson et al., 1990, Mol. Cell Biol. 10:4854–4862). Of the four members of the GATA-binding protein family (Orkin, S. H., supra; Arceci et al., 1993, Mol Cell Biol 13: 2235–2246), GATA-2 has been cloned from endothelial cells and been shown to regulate endothelin-1 gene expression in this cell type (19, 20). However, GATA-2 is expressed in many cell types, suggesting that an endothelial cell-specific coactivator may interact with GATA-2 to mediate endothelial cell-specific gene expression (Dorfman et al., supra; Lee et al., 1991, J. Biol. Chem. 266:16188–16192). For example, a B cell-specific coactivator that interacts with a universal trans-acting factor, Oct-1, has been shown to mediate B cell-specific gene expression (Luo et al., 1992, Cell 71:231–241).

Although there is an atypical GATA site within EN316 (SEQ ID NO:1), DNase I footprinting failed to show protein binding to this site. Furthermore, deletion of this site did not affect enhancer activity (FIG. 6). This absence of effect suggests that the atypical GATA consensus sequence is not the functional motif in EN316. Two protein binding motifs were identified in EN316, EnI (SEQ ID NO:2) and EnII (SEQ ID NO:3), using DNase I footprinting analysis (FIG. 4); deletion experiments (FIG. 6) revealed that each sequence has a functional effect on DNA transcription.

Further study of EnII indicated that the migration pattern of BI (FIG. 5B) generated by nuclear extract from BAEC differed from that generated by nuclear extracts from HeLa and 3T3 cells. This difference suggested the presence of an endothelial cell-specific trans-acting factor but does not exclude the possibility that a universal trans-acting factor binds to the HB-EGF enhancer and mediates its endothelial cell-specific function by interacting with an endothelial-specific coactivator (Luo et al., supra).

Use

The discovery and isolation of cis-acting elements and trans-acting factors that regulate HB-EGF gene expression forms the basis of the novel therapeutic approaches to arteriosclerosis and other vascular diseases described in the examples below.

EXAMPLE 1

Endothelial cell-specific DNA transcription

The invention includes gene therapy for arteriosclerosis. The novel endothelial cell-specific enhancer of the invention can be used to express foreign genes, e.g., genes which encode heterologous proteins, in cells of the blood vessel wall for gene therapy of inherited vascular diseases as well as arteriosclerosis. For example, thrombolytic agents can be expressed under the control of the HB-EGF enhancer for expression by vascular endothelial cells in the affected blood vessels, i.e., vessels occluded by aberrant blood clots. Other heterologous proteins, e.g., proteins which inhibit smooth muscle cell proliferation, e.g., interferon-γ, atrial natriuretic polypeptide, may be specifically expressed in endothelial cells to ensure the delivery of these therapeutic peptides to an arteriosclerotic lesion or an area at risk of developing an arteriosclerotic lesion, e.g., an injured blood vessel.

According to the invention, the HB-EGF enhancer is located sufficiently close to the DNA to be transcribed that it functions to enhance, i.e., upregulate, expression in an endothelial cell. For example, the enhancer may be located immediately upstream of the coding sequence start site, or up to approximately 2000 nucleotides upstream of the start site. It may alternatively be located downstream from the 3' end of the coding sequence, or within an intron between two exons of the coding sequence. The enhancer sequence may be inverse to the orientation observed relative to the naturally-occurring HB-EGF gene. Two or more copies of the enhancer may be arranged in tandem to increase expression of the heterologous protein to even higher levels. Two or more DNA sequences can also be arranged in tandem in the HB-EGF enhancer-containing DNA of the invention; transcription of both of these sequences would then be increased in endothelial cells.

The invention also includes antisense therapy for arteriosclerosis. Antisense therapy may be carried out by administering to an animal, e.g., a patient, DNA containing the HB-EGF enhancer and a DNA sequence which is transcribed into an antisense RNA. The antisense RNA may a short (generally at least 14 nucleotides, and up to 100 or more nucleotides) nucleotide sequence formulated to be complementary to a portion of a specific mRNA sequence. It is preferably located downstream from the enhancer of the invention and a functional promoter sequence. A poly A tail is typically located at the end of the antisense sequence to signal the end of the sequence. Standard methods relating to antisense technology have been described (Melani et al., Cancer Res. 51:2897–2901, 1991). Following transcription of the DNA sequence into antisense RNA, the antisense RNA binds to its target mRNA molecules within a cell, thereby inhibiting translation of the mRNA and down-regulating expression of the protein encoded by the mRNA. For example, an antisense sequence complementary to a portion of or all of the HB-EGF mRNA would inhibit the expression of HB-EGF, which in turn would inhibit the proliferation of vascular smooth muscle cells. The expression of other proteins involved in arteriosclerosis, e.g., cell adhesion molecules, e.g., endothelial leukocyte adhesion molecule, intercellular adhesion molecule and vascular cell adhesion molecule, may also be inhibited in a similar manner. Since smooth muscle cell proliferation contributes to the development of arteriosclerosis, such antisense therapy represents a promising approach the treatment of arteriosclerosis.

The claimed DNA may be introduced into target cells of an animal, e.g., a patient, by standard vectors and/or gene delivery systems. Suitable gene delivery systems may include liposomes, receptor-mediated delivery systems, naked DNA, and viral vectors such as herpes viruses, retroviruses, adenoviruses, and adeno-associated viruses among others. Standard methods for transfecting cells with isolated DNA are well known to those skilled in the art of molecular biology. Gene therapy and antisense therapy to prevent or decrease the development of arteriosclerosis may be carried out by directly administering the claimed DNA to a patient or by transfecting endothelial cells with the claimed DNA ex vivo and infusing the transfected cells into the patient.

DNA or transfected cells may be administered in a pharmaceutically acceptable carrier. Pharmaceutically acceptable carriers are biologically compatible vehicles which are suitable for administration to an animal, e.g., physiological saline. A therapeutically effective amount is an amount of the DNA of the invention which is capable of producing a medically desirable result in a treated animal. As is well known in the medical arts, dosages for any one patient depends upon many factors, including the patient's size, body surface area, age, the particular compound to be administered, sex, time and route of administration, general health, and other drugs being administered concurrently. Dosages will vary, but a preferred dosage for intravenous administration of DNA is from approximately $10^6$ to $10^{22}$ copies of the DNA molecule. Administration will generally be intravenously or parenterally; DNA may also be administered directly to the target site in the artery by catheter.

EXAMPLE 2

Inhibition of interactions of the HB-EGF enhancer with trans-acting factors

Another novel approach to the treatment of arteriosclerosis is the administration to a patient of compounds which associate with the HB-EGF enhancer, thus preventing the binding of a cell-specific trans-acting factor, e.g., a nuclear factor, to the enhancer DNA. Alternatively, a compound which associates with or alters the binding characteristics of a trans-acting factor may be used. In each case, binding of the trans-acting nuclear or cellular factor to the cis-acting DNA sequence is inhibited, resulting in a decrease in HB-EGF expression. A compound with the ability to block interactions at the HB-EGF enhancer may be administered to patients systemically or locally for the treatment of arteriosclerosis. To ensure the delivery of such compounds to the cytoplasm of the cell, they may be delivered in liposomes or other suitable formulations capable of mediating transfer of the compound across the cell membrane and into the cytoplasm of the cell.

Compounds with the ability to inhibit the association of a trans-acting endothelial cell-specific factor and the HB-EGF enhancer can be identified using the screening assays of the invention. A DNA fragment containing some or all of the HB-EGF enhancer, e.g., a fragment containing SEQ ID NO:1, SEQ ID NO:2, SEQ ID NO:3, or both SEQ ID NO:2 and SEQ ID NO:3 is contacted with a candidate compound. Binding of a compound to HB-EGF enhancer-containing DNA indicates that the compound has the ability to inhibit HB-EGF expression. Alternatively, both the HB-EGF enhancer-containing DNA and a trans-acting factor may be contacted with a candidate compound, followed by determination of the level of binding of the trans-acting factor to the HB-EGF enhancer-containing DNA. A decrease in the level of binding in the presence of the compound compared to the level of binding in the absence of the compound indicates that the compound inhibits the interaction of the trans-acting factor with the cis-acting enhancer DNA and thus, inhibits enhancer-dependent expression of HB-EGF. Binding of HB-EGF enhancer-containing DNA to trans-acting factor can be measured using the techniques described above, e.g., DNA footprinting or EMSA.

Other embodiments are within the following claims.

What is claimed is:

1. A substantially pure DNA comprising a heparin-binding epidermal growth factor-like growth factor (HB-EGF) enhancer, operably linked to a heterologous promoter and a sequence encoding a heterologous polypeptide, said enhancer comprising the nucleotide sequence of SEQ ID NO:1, said DNA lacking an HB-EGF promoter and and lacking a sequence encoding HB-EGF polypeptide, wherein said enhancer directs endothelial cell-specific expression of said heterologous polypeptide.

2. The DNA of claim 1, wherein said heterologous polypeptide is interferon-γ or atrial natriuretic polypeptide.

3. A vector comprising the DNA of claim 1.

4. A method of directing endothelial cell-specific expression of a polypeptide, comprising
   a) introducing into a cultured endothelial cell the vector of claim 3; and
   b) culturing said transformed cell under conditions suitable for expression.

5. A cultured endothelial cell containing the vector of claim 3.

6. A substantially pure DNA comprising a HB-EGF enhancer, operably linked to a heterologous promoter and a sequence encoding a heterologous polypeptide, said enhancer comprising the nucleotide sequence of SEQ ID NO:2, said DNA lacking an HB-EGF promoter and lacking a sequence encoding HB-EGF polypeptide, wherein said enhancer directs endothelial cell-specific expression of said heterologous polypeptide.

7. The DNA of claim 6, wherein said heterologous polypeptide is interferon-γ or atrial natriuretic polypeptide.

8. A vector comprising the DNA of claim 6.

9. A method of directing endothelial cell-specific expression of a polypeptide, comprising
   a) introducing into a cultured endothelial cell the vector of claim 8; and
   b) culturing said transformed cell under conditions suitable for expression.

10. A cultured endothelial cell containing the vector of claim 8.

11. A substantially pure DNA comprising a HB-EGF enhancer, operably linked to a heterologous promoter and a sequence encoding a heterologous polypeptide, said enhancer comprising the nucleotide sequence of SEQ ID NO:3, said DNA lacking an HB-EGF promoter and lacking a sequence encoding HB-EGF polypeptide, wherein said enhancer directs endothelial cell-specific expression of said heterologous polypeptide.

12. The DNA of claim 11, wherein said heterologous polypeptide is interferon-γ or atrial natriuretic polypeptide.

13. A vector comprising the DNA of claim 11.

14. A method of directing endothelial cell-specific expression of a polypeptide, comprising
   a) introducing into a cultured endothelial cell the vector of claim 13; and
   b) culturing said transformed cell under conditions suitable for expression.

15. A cultured endothelial cell containing the vector of claim 13.

16. A substantially pure DNA comprising a HB-EGF enhancer, operably linked to a heterologous promoter and a sequence encoding a heterologous polypeptide, said enhancer comprising both the nucleotide sequence of SEQ ID NO:2 and the nucleotide sequence of SEQ ID NO:3, said DNA lacking an HB-EGF promoter and lacking a sequence encoding HB-EGF polypeptide, wherein said enhancer directs endothelial cell-specific expression of said heterologous polypeptide.

17. The DNA of claim 16, wherein said heterologous polypeptide is interferon-γ or atrial natriuretic polypeptide.

18. A vector comprising the DNA of claim 16.

19. A method of directing endothelial cell-specific expression of a polypeptide, comprising
   a) introducing into a cultured endothelial cell the vector of claim 18; and
   b) culturing said transformed cell under conditions suitable for expression.

20. A cultured endothelial cell containing the vector of claim 18.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 316 base pairs
        ( B ) TYPE: nucleic acid
        ( C ) STRANDEDNESS: double
        ( D ) TOPOLOGY: linear ( i i ) MOLECULE TYPE: genomic cDNA ( x i ) SEQUENCE DESCRIPTION: SEQ ID NO:1:

```
TTTATCTTCT  TTTTCAGGC   CCTTCCTGTA  AAACCTGGCT  GACACACAAA  CCTAGCTGGG      60

GTGAGGCTCC  AGGTGTGATG  AAAGTTTGGA  GTTGCCCCAT  GAATGGGACT  GAGGCTGATG     120

TGGGGGTGAG  AAGGCGGAAG  GACAGAGCAT  GTGAAGGGAG  AAAGGCAGGC  TGGGGCAAGA     180

GAGCAGGGTG  TGACTCTGGC  GAGGGTGGGG  GAAAGGGGGT  GATTTGACCA  TGTGTCAGGA     240

AGTGTTTCTC  TCCACCCTCC  CCTGGGGAGA  GCCTTGACCC  CAAGGTGGCT  TTGTTTTGGG     300

GAAGCAGGTG  GCCAGG                                                         316
```

( 2 ) INFORMATION FOR SEQ ID NO:2:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: linear ( i i ) MOLECULE TYPE: genomic cDNA ( x i ) SEQUENCE DESCRIPTION: SEQ ID NO:2:

```
AAGGGGGTGA  TTTG                                                            14
```

( 2 ) INFORMATION FOR SEQ ID NO:3:

( i ) SEQUENCE CHARACTERISTICS:
        ( A ) LENGTH: 29 base pairs
        ( B ) TYPE: nucleic acid
        ( C ) STRANDEDNESS: double
        ( D ) TOPOLOGY: linear (ii) MOLECULE TYPE: genomic cDNA (xi) SEQUENCE DESCRIPTION: SEQ ID NO:3:

ATGTGGGGGT GAGAAGGCGG AAGGACAGA    29

(2) INFORMATION FOR SEQ ID NO:4:

(i) SEQUENCE CHARACTERISTICS:
    (A) LENGTH: 32 base pairs
    (B) TYPE: nucleic acid
    (C) STRANDEDNESS: double
    (D) TOPOLOGY: linear (ii) MOLECULE TYPE: genomic cDNA (xi) SEQUENCE DESCRIPTION: SEQ ID NO:4:

TTCTTGAGTG TCTTGTCTTG CTCACTCAGC CC    32